(12) United States Patent
Gruber et al.

(10) Patent No.: US 8,287,203 B2
(45) Date of Patent: Oct. 16, 2012

(54) PUMPING SYSTEM FOR AN ORAL COMPOSITION (75) Inventors: Paul Gruber, Sammamish, WA (US); Christian Mikula, Wernberg (AT); Christoph Winkler, Feistritz (AT)

(73) Assignee: Koninklijke Philips Electronics N.V., Eindhoven (NL)

( * ) Notice: Subject to any disclaimer, the term of this patent is extended or adjusted under 35 U.S.C. 154(b) by 1345 days.

(21) Appl. No.: 10/581,506

(22) PCT Filed: Dec. 9, 2004

(86) PCT No.: PCT/IB2004/052732
§ 371 (c)(1),
(2), (4) Date: May 23, 2007

(87) PCT Pub. No.: WO2005/058185
PCT Pub. Date: Jun. 30, 2005

(65) Prior Publication Data
US 2007/0275347 A1    Nov. 29, 2007

Related U.S. Application Data (60) Provisional application No. 60/528,627, filed on Dec. 11, 2003.

(51) Int. Cl.
*A46B 11/02* (2006.01)
(52) U.S. Cl. .................................. 401/188 R
(58) Field of Classification Search ............. 401/188 R, 401/270
See application file for complete search history.

(56) References Cited

U.S. PATENT DOCUMENTS

| 183,914 | A | | 10/1876 | Fitch |
|---|---|---|---|---|
| 2,946,725 | A | | 7/1960 | Norris et al. |
| 3,070,510 | A | | 12/1962 | Cooley et al. |
| 3,217,720 | A | | 11/1965 | Cyzer |
| 3,528,230 | A | | 11/1970 | Pader et al. |
| 3,862,307 | A | | 1/1975 | Giulio |
| 4,051,234 | A | | 9/1977 | Gieske et al. |
| 4,138,477 | A | | 2/1979 | Gaffar |
| 5,037,637 | A | | 8/1991 | Gaffar et al. |
| 5,180,577 | A | | 1/1993 | Polefka et al. |
| 5,309,590 | A | | 5/1994 | Giuliani et al. |
| 5,827,001 | A | * | 10/1998 | Taghavi-Khanghah ....... 401/145 |
| 5,909,977 | A | | 6/1999 | Kuo |
| 6,402,410 | B1 | | 6/2002 | Hall et al. |
| 6,406,207 | B1 | * | 6/2002 | Wiegner et al. ............... 401/272 |

FOREIGN PATENT DOCUMENTS

| WO | WO 96/19191 | 6/1996 |
|---|---|---|
| WO | WO 98/22079 | 5/1998 |
| WO | WO 99/43290 | 9/1999 |
| WO | WO 02/11641 | 2/2002 |
| WO | WO 02/41801 | 5/2002 |
| WO | WO 02/41802 | 5/2002 |
| WO | WO 02/064056 | 8/2002 |
| WO | WO 2004/032674 | 4/2004 |

* cited by examiner

*Primary Examiner* — David Walczak (57) ABSTRACT

A pumping system for an oral composition, having selected rheological properties, useful in oral treatment. The pumping system has defined rheological characteristics to move such an oral composition from a reservoir to an outlet of the system at a given rate.

20 Claims, 1 Drawing Sheet

PUMPING SYSTEM FOR AN ORAL COMPOSITION

CROSS REFERENCE TO RELATED APPLICATION

This application claims the benefit of U.S. provisional application Ser. No. 60/528,627 filed Dec. 11, 2003, which is incorporated herein whole by reference.

A pumping system for use with an oral composition in integrated oral treatment systems.

Recently, electric toothbrushes have become very popular with consumers and dentists alike. These devices are thought to provide better cleaning and massaging of the oral surfaces than traditional manual brushing. However, electric toothbrushes still require the dispensing of dentifrice onto the bristles prior to use. Commencement of brushing quickly results in a decrease of the concentration of dentifrice on the bristles, and possibly results in lower than expected cleaning of the tooth surfaces.

As a result, it is desirable to have an oral treatment system that comprises an oral composition that is dispensed through the bristle head and onto the bristles during brushing, either automatically, or at will. Such an idea is not new. For example, U.S. Pat. No. 3,217,720 discloses a toothbrush with a liquid dentifrice container. U.S. Pat. No. 5,909,977 discloses a dentifrice-dispensing toothbrush utilizing a refillable cartridge for storing dentifrice material and a compressible elastic button for pumping dentifrice material to the brush head. Further development of this idea includes the use of hollow bristles through which the dentifrice flows as disclosed in U.S. Pat. No. 5,309,590.

However, integration of this type creates new problems with regard to the rheological profile of the integrated oral composition. The oral composition is preferably pumped from a storage reservoir to the place of application through some form of tubing. In a toothbrush, the toothbrush neck needs to be less than a certain maximum diameter and greater than a certain minimum length to allow it to be comfortably used in the mouth. This restriction in the size of the neck necessarily restricts the maximum cross-sectional area and minimum length of the tubing used within to deliver the composition to the head of the toothbrush from the reservoir. This limitation on the cross-sectional area of the tubing results in high shear rates being developed as the oral composition is pumped through the tube, increasing the pressure required to transport the oral composition. Furthermore, toothbrushes necessarily have a limited pumping pressure, either due to power requirements in electrically operated pumping systems, or due to the maximum amount of force that can be applied conveniently by a consumer on manually operated pumps. Thus, the composition must have a specific rheological profile to allow it to be pumped through given tubing whilst minimizing the pressure requirement of the pumping system.

Furthermore, available oral compositions are not optimized for use with oral treatment systems, and may lead to too little or excessive toothbrush head pressure being applied to the oral tissues by the consumer to clean the teeth. Application of too little or excessive pressure to the bristle head may result in the cleaning efficiency of the oral treatment system being reduced.

Therefore, it is desirable to provide compositions for use in oral treatment systems that can be easily pumped through tubes of given diameter and length. Furthermore, it is also desirable to provide an oral treatment system comprising dentifrice compositions that have rheological properties that enable the composition to be easily pumped, yet also allow it to be retained within the bristles when dispensed. Further still, it is desirable to provide a kit containing the apparatus required to use an oral composition in an oral treatment system.

Additionally, it is desirable to provide oral compositions optimized for use in oral treatment systems that enables the manipulation of and pressure exerted by the consumer on the oral treatment system when used in the mouth.

Still further, it is desirable to provide a pumping system, including a pump and tubing of selected cross-sectional area, configuration and length, which can easily pump an oral composition which is retained within the bristles when dispensed.

These and other objects of the present invention will become more readily apparent from consideration of the following summary, detailed description and examples.

Accordingly, the present invention, in one aspect, is a pumping system for pumping an oral composition used in the treatment of the oral cavity, comprising: a pumping system for moving an oral composition which is useful in the treatment of the oral cavity, having a selected viscosity, from a reservoir of an oral treatment system to an outlet of the system, the pumping system including a pump and a fluid pathway for the oral composition to reach the outlet, wherein the pump is so characterized and the pathway has an internal cross-sectional area (A) within the range of 0.25 mm² to 16 mm² and a length (y) within the range of 100 mm to 200 mm and is otherwise so characterized by such a cross-sectional shape and cross-sectional uniformity along its length that an oral composition with a minimum viscosity of 10 Pa·s at a shear rate of 1 s$^{-1}$ and a maximum viscosity not greater than η(in Pa·s) at a shear rate γ(in s$^{-1}$) defined by the equations $$\eta = \frac{250A^2}{4y} \text{ and } \gamma = \frac{2500}{A^{3/2}}$$

can be moved to the outlet by the pump at a flow rate of at least 0.1 ml/second.

In another aspect, the invention is a system for treatment of the oral cavity, comprising an oral composition suitable for treatment of the oral cavity; a reservoir for the oral composition; and a pumping system for moving the oral composition from the reservoir to an outlet of the treatment system, the pumping system including a pump member and fluid pathway tube for the oral composition to reach to the outlet, wherein the pump is so characterized in the fluid pathway tube has an internal cross-sectional area (A) within the range of 0.25 mm to 16 mm² and a length (y) within the range of 100 mm to 200 mm and is otherwise so characterized by such a cross-sectional shape and uniformity of cross-sectional configuration along its length relative to an oral composition with a minimum viscosity of 10 Pa·s and a shear rate of 1 s$^{-1}$ and a maximum viscosity not greater than η(in Pa·s) at a shear rate γ(in s$^{-1}$) defined in the following equations $$\eta = \frac{250A^2}{4y} \text{ and } \gamma = \frac{2500}{A^{3/2}}$$

that said composition can be moved to the outlet by the pump at a flow rate of at least 0.1 ml/second.

Still another aspect of the invention is a method of treatment of the oral cavity, comprising the steps of: moving an oral composition suitable for treatment of the oral cavity with a pumping system from a reservoir to an outlet of an oral treatment system, the oral treatment system comprising a toothbrush having a brushhead with an outlet suitable for insertion into the oral cavity, the pumping system including a pump and a fluid pathway for an oral treatment composition to reach the outlet, wherein the pump is so characterized and the fluid pathway tube has an internal cross-sectional diameter (A) within the range of 0.25 mm² to 16 mm² and a length (y) within the range of 100 ml to 200 ml and is otherwise so characterized by such a cross-sectional shape and uniformity of cross-sectional configuration and length that the oral composition is moved to the outlet at a flow rate of at least 0.1 ml/second, wherein the oral composition has a minimum viscosity of 10 Pa·s and a shear rate of 1 s$^{-1}$ and a maximum viscosity not greater than η(in Pa·s) at a shear rate γ(s$^{-1}$) defined by the following equation:

$$\eta = \frac{250A^2}{4y} \text{ and } \gamma = \frac{2500}{A^{3/2}}.$$

All parts, percentages and proportions referred to herein and in the appended claims are by weight of the total oral composition unless otherwise indicated. All measurements are made at 25° C. on the total oral compositions unless otherwise indicated. Viscosity as used herein is measured using a Carrimed CSL$^2$ 100 rheometer with a 2 cm diameter parallel plate measuring system and a 500 micron gap between the plates.

Figure 1:
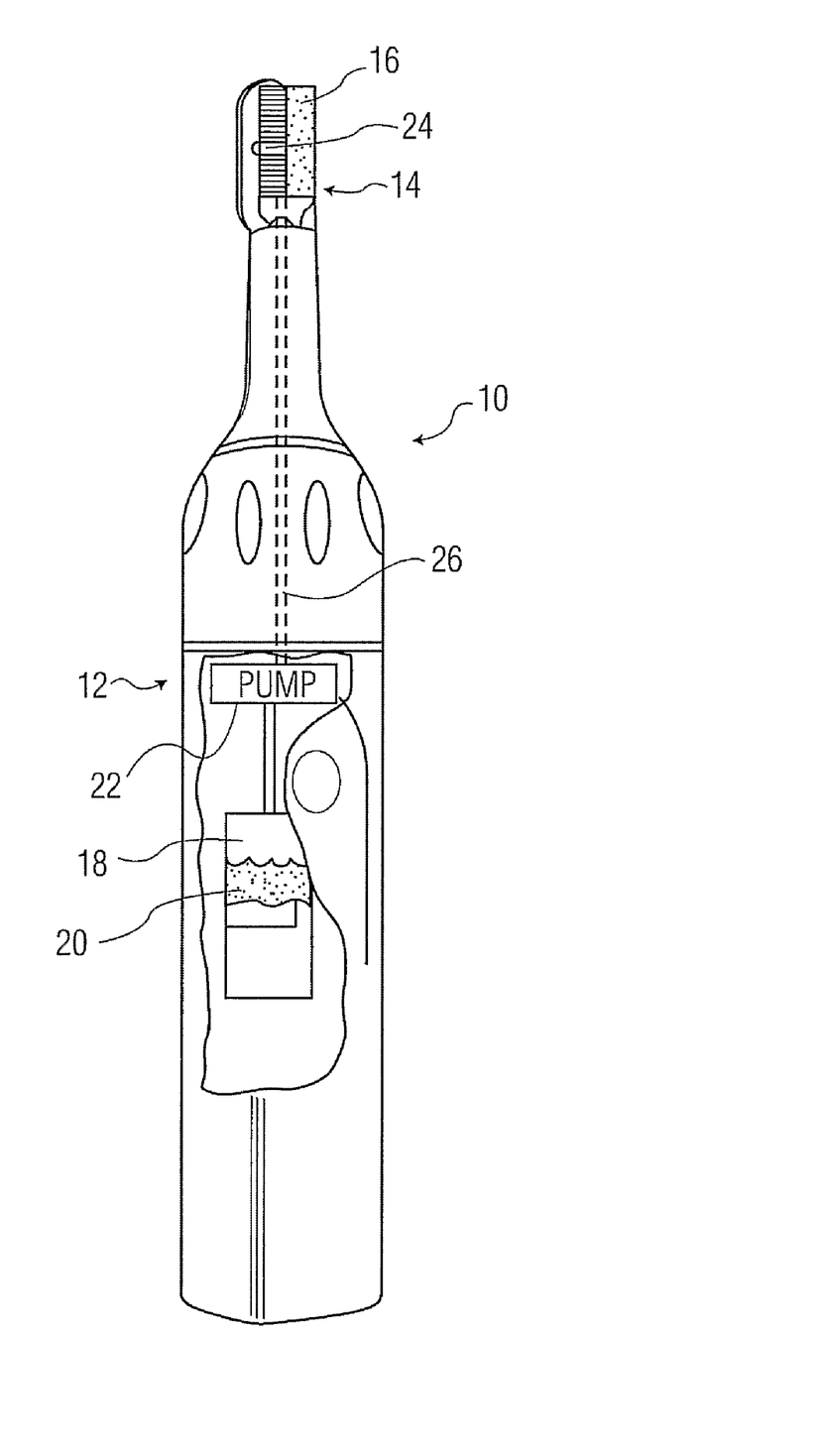
FIG. 1 shows a toothbrush which includes the pumping system of the present invention.

Initially, referring to FIG. 1, the system of the present invention is useful in a power toothbrush, shown generally at 10. The power toothbrush includes a housing 12 and brushhead shown generally at 14 with a bristle field 16 extending therefrom. Contained within the housing 12 is a reservoir 18 which contains an oral composition 20 useful in the treatment of the oral cavity. A pump 22 connects the reservoir 18 to an outlet 24 in the brushhead 14 for exit of the oral composition, via a fluid pathway tube 26. The above structure is described in more detail in the following paragraphs.

The oral compositions of the present invention are suitable for use in oral treatment systems wherein the oral composition is contained within a reservoir and is pumped from the reservoir to an outlet via a tube. They have viscosities that are optimized for transport via tubes of given diameter and length via relatively low force pumping means. Relatively low force means that the pumping force required is not sufficiently large to require high power input with regard to an electrically driven pump, or require exertion of high force from the finger of the user on the actuator of the pump. Relatively low force to transport the oral compositions refers to a force that is less than 100 N being required to drive the pump to attain the delivery rates indicated.

The oral composition for use herein enables the delivery of the oral composition through defined tube cross-sectional areas and lengths at a flow rate of at least 0.1 ml/s, preferably 0.2 ml/s. This is advantageous in allowing quick and efficient transport of the oral composition from the reservoir to the applicator head. The oral compositions for use herein may be Newtonian compositions, or shear thinning compositions, preferably shear thinning, such that as the shear rate, and therefore shear stress, is increased, the viscosity of the oral composition progressively lowers. The use of the oral composition in the oral treatment system herein allows efficient delivery of the oral composition to the applicator and its retention within the applicator, without requiring multiple applications or negatively influencing the aesthetics of the product.

Oral Treatment System

Toothbrush

The oral compositions of the present invention are suitable for use in a wide variety of oral treatment systems, such as integrated toothbrushes and electric toothbrushes. An exemplary oral treatment system is disclosed in WO 02/064056 A1 and U.S. Pat. No. 6,402,410 B1. Such systems comprise a reservoir, an applicator and means for transporting the oral composition from the reservoir to the applicator. Preferably, the oral treatment system is a hand-held portable device suitable for use with one hand. The oral treatment system preferably comprises a unitary housing that can be comfortably gripped in the user's hand, the housing preferably comprising the reservoir and the means for transporting the oral composition.

Reservoir

The system of the present invention comprises a reservoir for storing oral compositions. The reservoir may be fixedly or removably attached to the treatment system. Preferably the reservoir is replaceably removable from the housing, for example, to allow the reservoir to be refilled and the reservoir reinserted, or for the reservoir to be replaced by one of substantially similar construction that may comprise further quantities of oral composition. Any suitable reservoir may be utilized in the present invention. It should be understood that the reservoir utilized may be fully or partially internal to the housing of the treatment system, or fully or partially internal to the housing.

Non-limiting examples of suitable reservoirs include positive displacement-type reservoirs that are generally rigid-walled, such as a cartridge, and also include pump-evacuated type reservoirs that are generally soft-walled, such as sachets, bladders and blisters. Preferably, the reservoir is of the soft-walled, pump-evacuated type, more preferably a sachet. The reservoir may be manufactured from materials suitable to the application, known to those skilled in the art. For example, positive displacement-type reservoirs may be made from metal, rigid plastic and other suitably hard materials. Soft-walled, pump-evacuated reservoirs are preferably manufactured out of soft, pliable plastics, such as PET, PE, metalized PE, laminated aluminum and other suitable materials known to those skilled in the art. Preferably, the reservoir defines an internal volume of from 5 ml to 25 ml.

In an embodiment, the reservoir comprises means for attachment to the pump. This is desirable to allow the reservoir to be attached to the pump, for example when a replacement reservoir is being attached to the oral treatment system. In another embodiment, the reservoir may comprise the pumping means and means for attachment to the transporting tube. This is advantageous to allow the reservoir and pump to be replaced at the same time as a single unit. Suitable examples of the means for attachment of the reservoir to the pump include snap-lock fittings, gasket seals, bayonet and screw fittings.

In a further embodiment of the invention, provision may be made for in situ refilling of the reservoir from a separate refill cartridge, external to the housing of the system, which is provided either with the system, or as a separate item. This can be advantageous where the volumes of composition consumed during treatment are relatively large, and it would be costly or wasteful to throw away an internal reservoir each time it was emptied. The external refill cartridge may form part of a base station that additionally performs the function of providing a holder for the housing of the treatment system. Where the treatment system comprises electric means, the base station may additionally comprise recharging means for recharging a rechargeable battery within the treatment system.

Pump and Tubing

The oral treatment system of the present invention comprises means for transporting the oral composition from the reservoir to the applicator. Means for transporting the oral compositions may comprise a pump and/or tubing. Preferably, the oral treatment system comprises a pump to provide mechanical pressure to transport the oral compositions from the reservoir to the applicator. The pump may comprise an electronically controlled pump or, for example, a resilient push-button operated mechanical pump placed over the reservoir, or in line with a tube leading from the pump to the reservoir. Preferably, the pump comprises a positive displacement pump. Positive displacement pumps (see, for example p. 155 *Chemical Engineering*, Vol. 6, Design, R. K. Sinnott, Permagon Press, 1983) cover a variety of different designs of pumps in which material cannot back-flow through the pump when it is not being activated. Specific positive displacement pump designs suitable for use in a device such as this include peristaltic pumps, pistons and diaphragm pumps.

Diaphragm pumps herein typically comprise a pump body in which is contained the pump chamber (a void which may be filled with the product to be pumped), a pump activator consisting of an elastomeric membrane which forms the surface of the pump chamber, an inlet valve and an outlet valve. The pump activator may additionally comprise a spring to aid its return to the maximum pump chamber volume following depression. The pump body also includes an inlet nozzle with channel connected to inlet valve and an outlet nozzle with channel connecting to the outlet valve. The inlet valve is positioned between the inlet nozzle and the pump chamber and opens when the pressure inside the pump is lower than that on the inlet side of the valve, and closes when the pressure in the pump is higher than that on the inlet side of the valve. The inlet valve typically consists of an elastic material with the ability to spring shut on removal of reduced pressure in the chamber; a suitable material is PET. The outlet valve is positioned between the pump chamber and the outlet nozzle, and opens when the pressure inside the pump is higher than that on the outlet side of the valve, and closes when the pressure in the pump is lower than that on the outlet side of the valve. The outlet valve typically has similar properties to the inlet valve. The valves may be mounted onto a valve housing to support their structure and ensure that they can only open in one direction.

The activator, when depressed, causes the volume of the pump housing to decrease, pressure in the pump housing to increase, and product to be expelled through the outlet valve. The activator is sprung to allow it to recover to maximum volume when released. When the activator is released, the volume of the pump housing increases, causing the pressure in the housing to decrease and product to be sucked into the pump housing through the inlet valve. The activator typically consists of a thermoplastic elastomer, e.g. TPE (polyetherester).

In another embodiment, the pump may comprise a piston. A piston such as a syringe negates the need for a pump to be refilled with product. Preferred herein are diaphragm pumps.

The oral treatment system herein comprises means to transport the oral composition from the reservoir via the pump to the applicator. Suitable transport means include tubes. Non-limiting examples of tubes include silicone tubing, molded plastic channels and plastic tubing. Preferably, the tube has a sufficiently small internal cross-sectional area to allow it to be contained within the neck of the applicator without increasing the diameter of the neck of the applicator itself. The internal cross-section of the internal surface of the tube perpendicular to the longitudinal axis can define any closed shape, such as for example, a circle, an oval, or a polygon such as a square or rectangle.

In one embodiment, the tube has a sufficiently small internal cross-sectional area so as to be contained within the neck of the applicator along with a drive shaft for the motorized manipulation of the applicator head, the neck of the applicator being sufficiently narrow so as to maintain the ergonomics of the applicator. The internal cross-sectional area of the tube is preferably from 0.0025 mm$^2$ to 25 mm$^2$. More preferably, the internal cross-sectional area of the tube is from 0.01 mm$^2$ to 20.25 mm$^2$, more preferably still from 0.25 mm$^2$ to 16 mm$^2$. Yet more preferably still, the internal cross-sectional area of the tube is from 0.5 mm$^2$ to 10 mm$^2$.

Furthermore, the tube requires a length such that the reservoir and pump can be positioned at a distance from the applicator head so that the pump can be easily activated by the hand holding the oral treatment system. Preferably, the tubing has a length of from 10 mm to 300 mm, more preferably, from 50 mm to 250 mm, more preferably still, from 100 mm to 200 mm. Yet more preferably, the tube length is from 120 mm to 180 mm.

Additionally, the tube for use herein has a length to internal cross-sectional area (y:A) ratio of at least 1:1 mm$^{-1}$, preferably, at least 2:1 mm$^{-1}$. Where the tube has multiple different internal cross-sectional areas, the internal cross-sectional area used to determine the minimum length allowable by the above ratio shall be the smallest internal cross-sectional area of the tube. Where the tube expands under the flow of the oral composition, the internal cross-sectional area used to determine the minimum length according to the above ratio is that area defined by the maximum expansion of the tube.

Applicator

The oral treatment system of the present invention includes an applicator for applying the oral composition to the oral cavity. The applicator may be fixedly or releasably attached to the housing of the oral treatment system. Preferably, the applicator is releasably attached to the applicator. This is advantageous to allow replacement of the applicator with one of substantially similar construction without requiring the entire oral treatment system to be replaced. The applicator may be any device suitable for applying the oral compositions herein to the teeth or oral soft tissues, and may comprise a neck portion extending from the attachment means and terminating in a head portion that comprises an application surface that may be a brush or a sponge. Preferably, the applicator head comprises a brush. Typically, the neck portion has a length of from 20 mm to 100 mm and a diameter from 5 mm to 115 mm.

In addition to the tube, the applicator may comprise means for driving a motorized applicator head. Examples of such means include a drive shaft or gear arrangement.

Oral Composition

Viscosity

The oral composition of the present invention is a fluid composition having a select viscosity profile. Without wishing to be bound by theory, it is believed that the pressure required to pump an oral composition through a tube of given internal cross-sectional area and length is proportional to the viscosity of the oral composition at a shear rate defined by the tube size. Due to the limitations of pumping pressure, either to enable energy minimization in the case of electrically powered pumps, or to prevent excessive force requirement for manually operated pumps, the oral compositions of the present invention must have a viscosity at 25° C. not greater than η(in Pa·s) at shear rate γ(in s⁻¹), wherein η and γ are defined by the equations:

$$\eta = \frac{250A^2}{4y} \text{ and } \gamma = \frac{2500}{A^{3/2}};$$  Equation 1 and wherein A and y are, respectively, the internal cross-sectional area (mm2) and length (mm) of the tube used to transport the oral composition from the reservoir to the applicator head via a pump. Oral compositions having a viscosity of less than η at a shear rate γ will be suitable for pumping through a tube defined in terms of A and y above. Where the tube has multiple different internal cross-sectional areas, the viscosity shall be calculated as though the entire length of the tube (y) has an internal cross-sectional area (A) equal to the smallest internal cross-sectional area of the tube. Where the tube expands when the product contained within is pumped along its length, the cross-sectional area shall be determined as the area at the maximum expansion of the tube.

Table 1 below presents examples of preferred tube length and internal cross-sectional area combinations for use in the oral treatment system of the present invention, and the required viscosity limits for an oral composition for use therein according to equation 1.

TABLE 1

| Area (mm²) | Length (mm) | | | | Shear Rate γ (s⁻¹) |
|---|---|---|---|---|---|
| | 50 | 100 | 120 | 150 | |
| | Maximum Viscosity (Pa · s) | | | | |
| 1 | 1.25 | 0.625 | 0.52083 | 0.41667 | 2500 |
| 4 | 20 | 10 | 8.33333 | 6.66667 | 312.5 |
| 9 | 101.25 | 50.625 | 42.1875 | 33.75 | 92.59259 |
| 16 | 320 | 160 | 1333.333 | 106.667 | 39.0625 |

Additionally, the oral compositions of the present invention have a viscosity at a shear rate of 20 s⁻¹ of from 0.001 Pa·s to 780 Pa·s, preferably from 0.1 Pa·s to 500 Pa·s, more preferably from 1 Pa·s to 100 Pa·s.

Furthermore, the oral compositions of the present invention further require a viscosity at 25° C. of at least 10 Pa·s at a shear rate of 1 s⁻¹. This minimum viscosity at a shear rate of 1 s⁻¹ is required to prevent the oral composition from running off the applicator head once pumped therethrough the tube. Preferably, the oral composition for use herein has a viscosity at 25° C. of at least 25 Pa·s at a shear rate of 1 s⁻¹.

Furthermore, it is preferable that the oral compositions of the present invention have limited hysteresis, such that once the viscosity of the composition has been lowered by a shear stress, such as pumping through a tube, the composition returns rapidly to its low shear viscosity once the high shear stress has been removed.

Where the means for pumping the composition comprise a direct displacement pump, the oral composition preferably has a viscosity at 25° C. not greater than η(in Pa·s) at shear rate γ(in s⁻¹), wherein η and γ are defined by the equations:

$$\eta = \frac{10A^2}{y} \text{ and } \gamma = \frac{10{,}000}{A^{3/2}}.$$  Equation 2

Table 2 below presents examples of preferred tube length and internal cross-sectional area combinations for use in the oral treatment system of the present invention, and the preferred viscosity limits for an oral composition for use with a direct displacement pump therein according to Equation 2.

TABLE 2

| Area (mm²) | Length (mm) | | | | Shear Rate γ (s⁻¹) |
|---|---|---|---|---|---|
| | 50 | 100 | 120 | 150 | |
| | Maximum Viscosity (Pa · s) | | | | |
| 1 | 0.2 | 0.1 | 0.08333 | 0.06667 | 1000 |
| 4 | 3.1 | 1.6 | 1.33333 | 1.06667 | 1250 |
| 9 | 16.2 | 8.1 | 6.75 | 5.4 | 370.3704 |
| 16 | 51.2 | 25.6 | 21.3333 | 17.0667 | 156.25 |

More preferably, where the means for pumping the composition comprises a positive displacement pump, the oral composition preferably has a viscosity at 25° C. not greater than η(in Pa·s) at shear rate γ(in s-1), wherein η and γ are defined by the equations:

$$\eta = \frac{6A^2}{y} \text{ and } \gamma = \frac{10{,}000}{A^{3/2}}.$$  Equation 3

Table 3 below presents examples of preferred tube length and internal cross-sectional area combinations for use in the oral treatment system of the present invention, and the preferred viscosity limits for an oral composition for use with a positive displacement pump therein according to Equation 3.

TABLE 3

| Area (mm²) | Length (mm) | | | | Shear Rate γ (s⁻¹) |
|---|---|---|---|---|---|
| | 50 | 100 | 120 | 150 | |
| | Maximum Viscosity (Pa · s) | | | | |
| 1 | 0.12 | 0.06 | 0.05 | 0.04 | 10000 |
| 4 | 1.92 | 0.96 | 0.8 | 0.64 | 1250 |
| 9 | 9.72 | 4.86 | 4.05 | 3.24 | 370.3704 |
| 16 | 30.72 | 15.36 | 12.8 | 10.24 | 156.25 |

More preferably, where the means for pumping the composition comprises a diaphragm pump, the oral composition preferably has a viscosity at 25° C. not greater than η (in Pa·s) at shear rate γ(in s⁻¹), wherein η and γ are defined by the equations:

$$\eta = \frac{3A^2}{y} \text{ and } \gamma = \frac{10{,}000}{A^{3/2}}.$$  Equation 4

Table 4 below presents examples of preferred tube length and internal cross-sectional area combinations for use in the oral treatment system of the present invention, and the more preferred viscosity limits for an oral composition for use therein according to equation 4.

TABLE 4

| Area (mm²) | Length (mm) | | | | Shear Rate $\gamma$ (s$^{-1}$) |
| --- | --- | --- | --- | --- | --- |
| | 50 | 100 | 120 | 150 | |
| | Maximum Viscosity (Pa · s) | | | | |
| 1 | 0.06 | 0.03 | 0.025 | 0.02 | 1000 |
| 4 | 0.96 | 0.48 | 0.4 | 0.32 | 1250 |
| 9 | 4.86 | 2.43 | 2.025 | 1.62 | 370.3704 |
| 16 | 15.36 | 7.68 | 6.4 | 5.12 | 156.25 |

Oral compositions having viscosities within the limits defined by the above equations are excellent for use as oral treatment systems comprising means for pumping the oral composition, wherein the oral composition is pumped from a reservoir to the applicator via a tube. Compositions with viscosities above those defined in the present application are too viscous to be efficiently pumped through a tube of defined diameter and length. While these compositions may flow through a tube of the defined internal cross-sectional area and length, the force required to effectively transport these compositions with an efficient delivery flow rate is above that which can be efficiently supplied by a battery operated pump, or from manual manipulation of a pump activator by the consumer.

It is understood that instruments used to measure shear stress and shear rate (such as the Carrimed CSL$^2$ 100 rheometer used herein) are unable to attain some of the shear rates indicated by the equations for Y. In these instances, the viscosity of the oral composition at those shear rates is determined using the Herschel-Bulkley model. The shear stress of the oral composition is determined as a function of shear rate over a range of shear rates from 0 to 450 s$^{-1}$, or the maximum shear rate that can be applied to the oral composition without it becoming partially fractured, using a minimum of 40 evenly distributed shear rates within the range. The data is modeled by fitting the equation:

$$\tau = \tau_0 + \kappa \gamma^n,$$

wherein $\tau$ is the shear stress, $\tau_0$ is the yield stress, $\gamma$ is the shear rate, $\kappa$ is the consistency (the viscosity at 1 s$^{-1}$) and n is shear index. Once the values of $\tau_0$, $\kappa$ and n have been determined, the following equation is applied at the shear rate required to predict the viscosity of the oral composition at the high shear rate:

$$\eta = (\tau_0 \times \gamma^{-1}) + (\kappa \gamma^{n-1}).$$

Additionally, it is preferable that the oral composition for use in the present invention has a viscosity such that, once the pump, by its activation has been purged of the oral composition contained therein, the oral composition has a flow rate into the pomp of at least 0.2 ml/s, wherein the pump return force is less than 100 N. This is desirable to allow the pump to refill efficiently following dispensing of the product.

Additionally, it is preferable that the oral composition of the present invention, when diluted to a 16.67% slurry in water, has a viscosity of greater than 0.1 Pa·s at a shear rate of 1 s$^{-1}$. This is advantageous to provide an oral composition which, when diluted in the oral cavity, has a viscosity that is high enough to enable its retention in the oral cavity without excessive manipulation or pressure application of the applicator by the consumer. More preferably, the oral composition for use according to the present invention has a viscosity when diluted to a 16.67% slurry in water of greater than 0.2 Pa·s at a shear rate of 1 s$^{-1}$, more preferably still greater than 0.3 Pa·s at a shear rate of 1 s$^{-1}$. It has been found that oral compositions with dilution viscosities greater than 0.1 Pa·s at a shear rate of 1 s$^{-1}$ induce greater consumer compliance and better cleaning efficiency. It is believed that this is a result of less pressure being exerted by the oral treatment system on the oral tissues by the consumer to retain the diluted composition in the mouth. Reduction of the exerted pressure results in a better and more efficient cleaning action, and decreased irritation of the oral tissues. These two features result in improved consumer experience and therefore increase consumer compliance.

It has been found that the rheology of the oral composition is affected by the types and levels of thickeners, and also the types and levels of optional ingredients. It is known by those skilled in the art that different thickeners may be used at different levels to provide similar viscosity at one shear rate. However, these thickening systems display differing viscosity profiles over a range of shear rates. Some systems, such as those comprising synthetic hectorite clay, display thixotropic properties, yet are desirable, as they are highly shear thinning. Other thickeners do not shear thin sufficiently to enable their use herein. To maintain the shear thinning properties of the oral composition, it is preferable to avoid high levels of materials that excessively increase the high-shear viscosity. Examples of such materials include any Newtonian liquids, such as glycerin and hydrogenated starch hydrolysates (also known as hydrogenated glucose syrup). These materials, while being desirable as humectants and optional ingredients, when added at high levels can alter the thinning properties of the composition such as to render it unsuitable for use herein. Most liquid ingredients are thicker than the water they are usually replacing. This includes other humectants, such as propylene glycol and polyethylene glycols (PEG). If replacing water with one of these ingredients, the oral composition will have a higher viscosity at both high and low shear rates.

Additionally, it is preferable to avoid high levels of particulate solids, such as abrasives. These materials reduce the amount of shear thinning in the oral composition, making them unsuitable for transport via a pump and tube. It has been found that oral compositions comprising high levels of particulate solids are sometimes unable to be drawn into the pump from the reservoir, resulting in the pump becoming blocked.

Thickeners

Thickeners suitable for the present invention include organic and inorganic thickeners, and mixtures thereof. Inorganic thickeners include hectorite and derivatives, hydrated silicas, ternary and quaternary magnesium silicate derivatives, bentonite and mixtures thereof. Preferred inorganic thickeners are hectorite and derivatives, hydrated silicas and mixtures thereof. Organic thickeners include xanthan gum, carrageenan and derivatives, gellan gum, hydroxypropyl methyl cellulose, sclerotium gum and derivatives, pallulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives, polyacrylates and derivatives, methyl cellulose and derivatives, ethyl cellulose and derivatives, agar and derivatives, gum arabic and derivatives, pectin and derivatives, chitosan and derivatives, resinous polyethylene glycols such as PEG-XM where X is >1, araya gum, locust bean gum, natto gum, co-polymers of vinyl pyrollidone with alkenes, tragacanth gum, polyacrylamides, chitin derivatives, gelatin, betaglucan, dextrin, dextran, cyclodextrin, methacrylates, microcrystalline cellulose, polyquatemiums, furcellaren gum, ghatti gum, psyilium gum, quince gum, tamarind gum, larch gum, tara gum, and mixtures thereof. Preferred are xanthan gum, carrageenan and derivatives, gellan gum, hydroxypropyl methyl cellulose, sclerotium gum and derivatives, pullulan, rhamsan gum, welan gum, konjac, curdlan, carbomer, algin, alginic acid, alginates and derivatives, hydroxyethyl cellulose and derivatives, hydroxypropyl cellulose and derivatives, starch phosphate derivatives, guar gum and derivatives, starch and derivatives, co-polymers of maleic acid anhydride with alkenes and derivatives, cellulose gum and derivatives, ethylene glycol/propylene glycol co-polymers, poloxamers and derivatives and mixtures thereof. More preferred are xanthan gum, carrageenan and derivatives, gellan gum, hydroxypropyl methyl cellulose, sclerotium gum and derivatives, pullulan, rhamsan gum, welan gum, konjac, curdlan, and mixtures thereof.

Amounts of thickeners may range from greater than 0.5% up to 4%, preferably greater than 0.5% up to 3%, more preferably greater than 0.5% up to 2% by weight.

As described above, compositions comprising bentonite clay and hectorite clays such as lapenite are highly shear thinning, and therefore desirable for use in the present invention. However, compositions comprising these thickeners display thixotropic properties. Compositions comprising the more preferred polysaccharide gums, such as xanthan gum and carrageenan, do not shear thin to the same extent as those comprising laponite or bentonite clay, but display less thixotropy following dispensing.

Surfactants

The oral composition of the present invention comprises greater than about 0.1% by weight of a surfactant or mixture of surfactants. Surfactant levels cited herein are on a 100% active basis, even though common raw materials such as sodium lauryl sulphate may be supplied as aqueous solutions of lower activity.

The surfactant is important for oral cleaning, both through removal of dirt from surfaces and in foam generation to suspend removed dirt. Suitable surfactant levels are from about 0.1% to about 15%, preferably from about 0.25% to about 10%, more preferably from about 0.5% to about 5% by weight of the total composition. Suitable surfactants for use herein include anionic, amphoteric, non-ionic, zwitterionic and cationic surfactants, though anionic, amphoteric, non-ionic and zwitterionic surfactants (and mixtures thereof) are preferred.

Useful anionic surfactants herein include the water-soluble salts of alkyl sulphates and alkyl ether sulphates having from 10 to 18 carbon atoms in the alkyl radical, and the water-soluble salts of sulphonated monoglycerides of fatty acids having from 10 to 18 carbon atoms. Sodium lauryl sulphate and sodium coconut monoglyceride sulphonates are examples of anionic surfactants of this type. Sodium lauryl sulphate is preferred. In preferred embodiments, the oral composition comprises at least about 0.125%, preferably at least about 0.5% anionic surfactant, more preferably at least about 2%.

Suitable cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; benzalkonium chloride; cetyl trimethylammonium bromide; diisobutylphenoxyethyl-dimethylbenzyl-ammonium chloride; coconut alkyltrimethylammonium nitrite; cetyl pyridinium fluoride; etc. Certain cationic surfactants can also act as germicides in the compositions disclosed herein.

Suitable nonionic surfactants that can be used in the compositions of the present invention can be broadly defined as compounds produced by the condensation of alkylene oxide groups (hydrophilic in nature) with an organic hydrophobic compound which may be aliphatic and/or aromatic in nature. Examples of suitable nonionic surfactants include the poloxamers; sorbitan derivatives, such as sorbitan di-isostearate; ethylene oxide condensates of hydrogenated castor oil, such as PEG-30 hydrogenated castor oil; ethylene oxide condensates of aliphatic alcohols or alkyl phenols; products derived from the condensation of ethylene oxide with the reaction product of propylene oxide and ethylene diamine; long chain tertiary amine oxides; long chain tertiary phosphine oxides; long chain dialkyl sulphoxides and mixtures of such materials. These materials are useful for stabilizing foams without contributing to excess viscosity build for the oral composition.

Zwitterionic surfactants can be broadly described as derivatives of aliphatic quaternary ammonium, phosphonium and sulphonium compounds, in which the aliphatic radicals can be straight chain or branched, and wherein one of the aliphatic substituents contains from about 8 to 18 carbon atoms and one contains an anionic water-solubilizing group, e.g. carboxy, sulphonate, sulphate, phosphate or phosphonate. Preferred zwitterionic surfactants include the betaine surfactants disclosed in U.S. Pat. No. 5,180,577.

Liquid Carrier Materials

The oral composition of this invention comprises greater than about 50% liquid carrier materials. Water is usually present. Water employed in the preparation of commercially suitable oral composition should preferably be deionized and free of organic impurities. Water generally comprises from about 10% to 50% by weight of the liquid dentifrice compositions herein. Preferably, the compositions include at least about 30% water, suitably from about 30% to about 50% water. These amounts of water include the free water which is added plus that which is introduced with other materials such as with sorbitol and with surfactant solutions.

Generally, the liquid carrier will further include one or more humectants. Suitable humectants include glycerin, sorbitol and other edible polyhydric alcohols, such as low molecular weight polyethylene glycols at levels of from about 15% to about 50%. To provide the best balance of foaming properties and resistance to drying out, the ratio of total water to total humectants is preferably from about 0.65:1 to 1.5:1, preferably from about 0.85:1 to 1.3:1.

Ethanol may also be present in the oral compositions. These amounts may range from 0.5 to 5%, optimally from 1.5 to 3.5% by weight. Ethanol can be a useful solvent and can also serve to enhance the impact of a flavor, though in this latter respect, only low levels are usually employed. Non-ethanolic solvents such as propylene glycol may also be employed. Also useful herein are low molecular weight polyethylene glycols.

Other Components

The oral composition herein will typically comprise a variety of other components, such as abrasives, fluoride ion sources, chelating agents, antimicrobials, thickeners, silicone oils and other adjuvants, such as preservatives and coloring agents.

Abrasives

The oral composition of the present invention may comprise a dental abrasive. Abrasives serve to polish the teeth and/or remove surface deposits. The abrasive material contemplated for use herein can be any material which does not excessively abrade dentine. Suitable abrasives include insoluble phosphate polishing agents, including various calcium phosphates, such as, for example, dicalcium phosphate, tricalcium phosphate, calcium pyrophosphate, beta-phase calcium pyrophosphate, dicalcium phosphate dihydrate, anhydrous calcium phosphate, insoluble sodium metaphosphate and the like. Also suitable are chalk-type abrasives, such as calcium and magnesium carbonates; silicas including xerogels, hydrogels, aerogels and precipitates; alumina and hydrates thereof, such as alpha alumina trihydrate; alominosilicates, such as calcined aluminum silicate and aluminum silicate, magnesium and zirconium silicates, such as magnesium trisilicate; and thermosetting polymerized resins, such as particulate condensation products of urea and formaldehyde, polymethylmethacrylate; powdered polyethylene and others, such as disclosed in U.S. Pat. No. 3,070,510, Dec. 25, 1962. Mixtures of abrasives can also be used. The abrasive polishing materials generally have an average particle size of from about 0.1 to about 30 microns, preferably from about 1 to 15 microns.

Silica dental abrasives of various types offer exceptional dental cleaning and polishing performance without unduly abrading tooth enamel or dentin. The silica abrasive can be precipitated silica or silica gels, such as the silica xerogels described in Pader et al., U.S. Pat. No. 3,538,230, issued Mar. 2, 1970; and DiGiulio, U.S. Pat. No. 3,862,307, issued Jun. 21, 1975, for example silica xerogels marketed under the trade name "Syloid" by W. R. Grace & Company, Davison Chemical Division. Suitable precipitated silicas include those marketed by INEOS under the trade names Sorbosil AC 43 and AC 33. Preferred are silicas that have an oil absorption of from 30 g per 100 g to 100 g per 100 g of silica. It has been found that silicas with low oil absorption levels are less structuring, and therefore do not build the viscosity of the oral composition to the same degree as those silicas that are more highly structuring, and therefore have higher oil absorption levels. As used herein, oil absorption is measured by measuring the maximum amount of linseed oil the silica can absorb at 25° C.

Suitable abrasive levels are from about 0% to about 20%, preferably less than 10%. Relatively low abrasive levels from 3% to 5% are preferred. It has been found that oral compositions with high levels of abrasive do not have rheological properties suitable for use in the present invention. Without wishing to be bound by theory, it is believed that oral-compositions comprising higher levels of abrasives, while having a good low-shear viscosity for stability once dispensed, do not thin sufficiently under higher shear rates to provide good pump refill and outflow characteristics.

Fluoride Ion Sources

For anticaries protection, a source of fluoride ion will normally be present in the oral composition. Fluoride sources include sodium fluoride, potassium fluoride, calcium fluoride, stannous fluoride, stannous monofluorophosphate and sodium monofluorophosphate. Preferred is sodium fluoride. Suitable levels provide from 25 to 2500 ppm of available fluoride ion by weight of the liquid dentifrice.

Chelating Agents

Another preferred optional agent is a chelating agent, of value as an anticalculus agent. Suitable chelating agents include organic acids and their salts, such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high. This results in tooth demineralization and is contrary to the objects and intentions of the present invention. Preferred chelating agents have a calcium binding constant of about 101 to 105 to provide improved cleaning with reduced plaque and calculus formation. The amounts of chelating agent suitable for use in the present invention are about 0.1% to about 2.5%, preferably from about 0.5% to about 2.5%, and more preferably from about 1.0% to about 2.5%. The tartaric acid salt chelating agent can be used alone or in combination with other optional chelating agents.

Another group of agents particularly suitable for use as chelating agents in the present invention are the soluble polyphosphates, polyphosphonates and pyrophosphates, which are useful as anticalculus agents. The pyrophosphate salts used in the present compositions can be any of the alkali metal pyrophosphate salts. An effective amount of pyrophosphate salt useful in the present composition is generally enough to provide at least 1.0% pyrophosphate ion, preferably from about 1.5% to about 6% of such ions. The pyrophosphate salts are described in more detail in Kirk & Othmer, *Encyclopedia of Chemical Technology*, Second Edition, Volume 15, Interscience Publishers (1968).

Also useful are the soluble polyphosphates, such as sodium tripolyphosphate and sodium hexametaphosphate. Other long chain anticalculus agents of this type are described in WO98/22079. Particularly preferred for use herein are sodium polyphosphate salts containing about 15 to about 25 phosphate units.

Still another possible group of chelating agents suitable for use in the present invention are the anionic polymeric polycarboxylates. Such materials are well known in the art, being employed in the form of their free acids or partially or preferably fully neutralized water-soluble alkali metal (e.g. potassium and preferably sodium) or ammonium salts. Additional polymeric polycarboxylates are disclosed in U.S. Pat. No. 4,138,477 to Gaffar and U.S. Pat. No. 4,183,914 to Gaffar et al., and include copolymers of maleic anhydride with styrene, isobutylene or ethyl vinyl ether, polyacrylic, polyitaconic and polymaleic acids, and solphoacrylic oligomers of MW as low as 1,000 available as Uniroyal ND-2.

Antimicrobials

Also useful for inclusion in the compositions of the present invention are antimicrobial agents. A wide variety of antimicrobial agents can be used, including stannous salts, such as stannous pyrophosphate and stannous gluconate; zinc salt, such as zinc lactate and zinc citrate; copper salts, such as copper bisglycinate; quaternary ammonium salts, such as cetyl pyridinium chloride and tetradecylethyl pyridinium chloride; bis-biguanide salts; and nonionic antimicrobial agents, such as triclosan. Certain flavor oils, such as thymol, may also have antimicrobial activity. Such agents are disclosed in U.S. Pat. No. 2,946,725, Jul. 26, 1960, to Norris et al., and U.S. Pat. No. 4,051,234, Sep. 27, 1977 to Gieske et al. Also useful is sodium chlorite, described in WO 99/43290, incorporated herein by reference.

Antimicrobial agents, if present, are typically included at levels of from about 0.01% to about 10%. It is preferred to keep the level of stannous and cationic antimicrobial agents to less than 5%, preferably less than 1% to avoid staining problems.

Preferred antimicrobial agents are non-cationic antimicrobial agents, such as those described in U.S. Pat. No. 5,037,637. A particularly preferred antimicrobial agent is 2',4,4'-trichloro-2-hydroxy-diphenyl ether (triclosan).

Silicone Oils

An optional ingredient in the present compositions is a silicone oil. Silicone oils can be useful as plaque barriers, as disclosed in WO 96/19191, incorporated herein by reference. Suitable classes of silicone oils include, but are not limited to, dimethicones, dimethiconols, dimethicone copolyols and amino-alkylsilicones, preferred silicone oils are selected from dimethicone copolyols and amino-alkylsilicones, more preferably from dimethicone copolyols. Silicone oils are generally present in a level of from about 0.1% to about 15%, preferably from about 0.5% to about 5%, more preferably from about 0.5% to about 3% by weight.

Other Adjuvants

Sweetening agents, such as sodium saccharin, sodium cyclamate, Acesulfame K, aspartame, sucrose and the like, may be included at levels from about 0.1 to 5% by weight. Other additives may also be incorporated, including flavors, preservatives, opacifiers and colorants. Typical colorants are D&C Yellow No. 10, FD&C Blue No. 1, FD&C Red No. 40, D&C Red No.33 and combinations thereof. Levels of the colorant may range from 0.0001 to 0.1%.

EXAMPLES

The following examples will more fully illustrate embodiments of this invention, Oral Composition tional uniformity along its length that the oral composition used with the pumping system having a minimum viscosity of 10 Pa·s at a shear rate of 1 s$^{-1}$ and a maximum viscosity not greater than $\eta$(in Pa·s) at a shear rate $\gamma$(in s$^{-1}$) defined as follows:

$$\eta = \frac{250A^2}{4y} \text{ and } \gamma = \frac{2500}{A^{3/2}}$$

can be moved to the outlet by the pump at a rate of at least 0.1 ml per second.

|  | Example # | | | | |
| --- | --- | --- | --- | --- | --- |
| Material Name | I Wt % | II Wt % | III Wt % | IV Wt % | V Wt % |
| Sorbitol (70%) | 43.97 | 41.9 | 56.0 | 41.9 | 52.0 |
| Glycerin | 10.0 | 10.0 | 10.0 | 10.0 | 10.0 |
| Sodium fluoride | 0.24 | 0.32 | 0.32 | 0.32 | 0.32 |
| Xanthan gum | 1.0 | 1.0 | 0.6 | 1.0 | 1.0 |
| Sodium alkyl sulphate, 28% | 9.0 | 9.0 | 9.0 | 9.0 | 9.0 |
| Precipitated silica | — | 3.0 | 10.0 | 10.0 | 5.0 |
| PEG-6 | 5.0 | 5.0 | 4.5 | 5.0 | — |
| PEG-12 | — | — | — | — | 3.0 |
| PEG-20 M | — | — | — | 1.3 | 4.0 |
| Triclosan | — | 0.3 | 0.3 | — | — |
| Sodium saccharin | 0.3 | 0.45 | 0.45 | 0.45 | 0.45 |
| Flavor | 1.7 | 1.7 | 1.7 | 1.9 | 1.7 |
| Preservative | 0.1 | 0.1 | 0.1 | 0.1 | 0.1 |
| CI 42090 FD&C Blue No. 1 | 0.002 | 0.002 | 0.002 | 0.002 | 0.002 |
| Water | to 100% | to 100% | to 100% | to 100% | to 100% |
| Viscosity at 1 s$^{-1}$ (Pa · s) | 47.3 | >10 | >10 | >10 | >10 |
| Viscosity at 20 s$^{-1}$ (Pa · s) | 3.4 | <780 | <780 | <780 | <780 |

The oral compositions of the examples above were incorporated into an oral treatment system comprising a reservoir, a pump and a tube and an applicator. The oral compositions were packaged in a vacuum-evacuated collapsible sachet made from heat-sealed aluminum-plastic laminate. The sachet was attached to the inlet nozzle of a diaphragm pump with a diaphragm chamber volume of 0.3 ml via a snap-lock connector. The outlet nozzle of the pump was connected to silicone tube with a circular cross-section, an internal cross-sectional area of 3.14 mm$^2$ and a length of 120 mm. The end of the silicone tube distal to the pump was finished with a silicone slit non-return valve in the head of a brush applicator. When the pump actuator was operated manually, the oral compositions of the examples above were dispensed at a flow rate of approximately 0.3 ml/s. The compositions above were effectively and efficiently dispensed without need of excessive force application by the user. Once dispensed, the oral attained an acceptable viscosity at 1 s$^{-1}$ rapidly.

The invention claimed is:

1. The combination of an oral composition used in the treatment of the oral cavity and a pumping system for pumping the oral composition, comprising:
an oral composition useful in the treatment of the oral cavity, the oral composition having a selected viscosity;
a pumping system for moving the oral composition from a reservoir of an oral treatment system to an outlet of the system, the pumping system including a pump and a fluid pathway for the oral composition to reach the outlet, wherein the pump is so characterized and the pathway has an internal cross-sectional, area (A) within the range of 0.25 mm$^2$-16 mm$^2$ and a length (y) within the range of 100 mm-200 mm and is otherwise so characterized by such a cross-sectional shape and cross-sec- 2. The pumping system of claim 1, wherein said rate is preferably approximately 0.2 ml per second.

3. The pumping system of claim 1, wherein the fluid pathways are flexible tubing and the internal cross-sectional area of the tubing is within the range of 0.5 mm$^2$ to 10 mm$^2$ and the length of the tubing is from 120 mm to 180 mm.

4. The pumping system of claim 1, wherein the pump is a positive displacement pump.

5. The pumping system of claim 4, wherein the positive displacement pump is a diaphragm pump.

6. The pumping system of claim 3, wherein the tubing has a length to internal cross-section area ratio of at least 1:1 ml$^{-1}$.

7. A system for treatment of the oral cavity, comprising:
an oral composition suitable for treatment of the oral cavity;
a reservoir for the oral composition; and
a pumping system for moving the oral composition from the reservoir to an outlet of the treatment system, the pumping system including a pump member and a fluid pathway tube for the oral composition to reach the outlet, wherein the pump is so characterized and the fluid pathway tube has a cross-sectional area (A) within the range of 0.25 mm$^2$ to 16 mm$^2$ and a length (y) within the range of 100 mm-200 mm and otherwise so characterized by a selected cross-sectional shape and uniformity of cross-sectional configuration along its length relative to the oral composition with a minimum viscosity of 10 Pa·s and a shear rate of 1 s$^{-1}$ and a viscosity not greater than $\eta$(in Pa·s) at a shear rate $\gamma$(in s$^{-1}$), defined in the following equations:

$$\eta = \frac{250A^2}{4y} \text{ and } \gamma = \frac{2500}{A^{3/2}}$$

that said composition can be moved to the outlet by the pump at a flow rate of at least 0.1 ml per second.

8. The system of claim 7, wherein the fluid pathway tube has an internal cross-sectional area within the range of 0.5 mm² to 10 mm² and a length within the range of 120 mm to 180 mm.

9. The system of claim 7, wherein the reservoir has an internal volume of between 5 ml and 25 ml.

10. The system of claim 7, wherein the flow rate is preferably 0.2 ml per second.

11. The system of claim 7, wherein the oral treatment system includes a hand-held toothbrush which can he gripped in the user's hand, wherein the housing contains the reservoir and the outlet is within a bristle portion of the toothbrush.

12. A method of treatment of the oral cavity, comprising the steps of:
moving an oral composition suitable for treatment of the oral cavity with a pumping system from a reservoir to an outlet of an oral treatment system, the oral treatment system comprising a toothbrush having a brushhead with an outlet suitable for insertion into the oral cavity, the pumping system including a pump and a fluid pathway tube for an oral treatment composition, wherein the pump is so characterized and the fluid pathway tube has an internal cross-section diameter (A) within the range of 0.25 mm² to 16 mm² and a length (y) within the range of 100 mm to 200 mm and is otherwise so characterized by a cross-sectional shape and uniformity of cross-sectional configuration that the oral composition is moved to the outlet at a flow rate of at least 0.1 ml per second, wherein the oral composition has a minimum viscosity of 10 Pa·s and a shear rate of 1 s⁻¹ and a maximum viscosity not greater than η(in Pa·s) at a shear rate γ(in s⁻¹), defined by the following equation $$\eta = \frac{250A^2}{4y} \text{ and } \gamma = \frac{2500}{A^{3/2}}.$$

13. The treatment method of claim 12, wherein said flow rate is approximately 0.2 ml per second.

14. The treatment method of claim 12, wherein the reservoir has an internal volume of between 5 ml and 25 ml.

15. The treatment method of claim 12, wherein the fluid pathway has a cross-sectional area within the range of 5 mm² to 10 mm² and a length within the range of 120 mm to 180 mm.

16. A kit for care of the oral cavity, comprising:
an oral composition which is useful in the treatment of the oral cavity; and
an oral treatment system which includes a reservoir for containing the oral composition, a fluid pathway and a pump for moving the oral composition from the reservoir through the fluid pathway to an outlet of the oral treatment system, wherein the pump is configured and arranged and otherwise so characterized and wherein the fluid pathway has a cross-sectional area (A) within the range of 0.25 mm² to 16 mm² and a length (y) within the range of 100 mm-200 mm and is otherwise so characterized by a selected cross-section shape and uniformity of cross-sectional configuration along its length relative to the oral composition which is moved there along and which has a minimum viscosity of 10 Pa·s, and a shear rate of 1 s⁻¹ and a viscosity not greater than η(in Pa·s) at a shear rate γ(in s⁻¹) defined in the following eqautions:

$$\eta = \frac{250A^2}{4y} \text{ and } \gamma = \frac{2500}{A^{3/2}}$$

that said composition is moved to the outlet of the oral treatment system by the pump at a flow rate of at least 0.1 ml per second.

17. The kit of claim 16, wherein the fluid pathway is a tube which has an internal cross-sectional area within the range of 0.5 mm² to 10 mm² and a length within the range of 120 mm to 180 mm.

18. The kit of claim 16, wherein the reservoir has an internal volume of between 5 ml and 25 ml.

19. The kit of claim 16, wherein the oral treatment system includes a hand held toothbrush having a housing which contains the reservoir and wherein the outlet of the oral treatment system is located within a bristle portion of the toothbrush.

20. The kit of claim 17, wherein the tube has a length to internal cross-sectional area ratio of at least 1:1 ml⁻¹.

* * * * *